(12) United States Patent
Blackwood et al.

(10) Patent No.: US 7,245,758 B2
(45) Date of Patent: Jul. 17, 2007

(54) WHOLE-WAFER PHOTOEMISSION ANALYSIS

(75) Inventors: Jeffrey Blackwood, Portland, OR (US); Tracy Myers, Clackamas, OR (US)

(73) Assignee: LSI Corporation, Milpitas, CA (US)

( * ) Notice: Subject to any disclaimer, the term of this patent is extended or adjusted under 35 U.S.C. 154(b) by 699 days.

(21) Appl. No.: 10/644,116

(22) Filed: Aug. 20, 2003

(65) Prior Publication Data

US 2005/0041849 A1    Feb. 24, 2005

(51) Int. Cl.
*G06K 9/00* (2006.01)
(52) U.S. Cl. .................................................. 382/145
(58) Field of Classification Search ............... 382/141, 382/145, 147, 149; 348/126
See application file for complete search history.

(56) References Cited

U.S. PATENT DOCUMENTS

| | | | | |
|---|---|---|---|---|
| 4,680,635 A | * | 7/1987 | Khurana | 348/79 |
| 4,755,874 A | * | 7/1988 | Esrig et al. | 348/126 |
| 5,970,167 A | * | 10/1999 | Colvin | 382/149 |
| 6,716,683 B1 | * | 4/2004 | Bruce et al. | 438/151 |

OTHER PUBLICATIONS

Trigg "The infrared photoemission microscope as a tool for semiconductor device failure analysis", IEEE, pp. 21-26, 1997.*
Khiam, et al "A new fluorescent and photoemission microscope for submicron VLSI IC failure analysis", IEEE, pp. 27-32.*

* cited by examiner

*Primary Examiner*—Daniel Miriam
(74) *Attorney, Agent, or Firm*—Trexler, Bushnell, Giangorgi & Blackstone Ltd.

(57) ABSTRACT

A method and system for collecting and analyzing photoemission data wherein illumination and photoemission images are acquired for a plurality of die, such as for each die on a wafer. Then, the images are overlaid, aligned, and assembled in a mosaic, thereby allowing analysis of the photoemission occurring across a plurality of die, such as across the entire wafer. Preferably, gathering this data allows statistical analysis of the photoemission such as analysis of commonly emitting locations to identify structures/cells that are sensitive to the manufacturing process.

10 Claims, 1 Drawing Sheet

WHOLE-WAFER PHOTOEMISSION ANALYSIS

BACKGROUND OF THE INVENTION

The present invention generally relates to the field of failure analysis and yield engineering, and more specifically relates to photoemission data collection.

Photoemission analysis is the technique of analyzing the photons emitted from an integrated circuit under various operating conditions. Most CMOS circuits consume very little power in a static state, hence emitting few photons. Depending on the type and size of a defect, a defective part may emit a large quantity of photons (light) which is detectable with specialized analysis equipment. Most photoemission occurs at the junction level of the device, in wavelengths in the infrared range. As silicon is transparent to infrared light, and due to the increasing number and density of metallization interconnect layers, one of the more effective methods of photoemission analysis involves imaging the die and analyzing the photoemission from the die under test from the back side of the wafer.

Current photoemission analysis techniques focus analysis on a single die/package or sub-circuit of an integrated circuit. The dataflow is illustrated in FIG. 1, and provides that an illuminated image of a die is acquired, power is applied to the Device Under Test (DUT), a photoemission image is acquired, and then the images are overlaid and aligned. This may be repeated for several die on the wafer, or on several packaged parts. Current photoemission techniques allow for the location and isolation of a photoemission site to within several microns accuracy. However, analysis on a die-by-die basis is a time-consuming process that limits the effectiveness of photoemission analysis as a yield management tool.

OBJECTS AND SUMMARY OF THE INVENTION

An object of an embodiment of the present invention is to provide a method and system wherein photoemission data is collected for a whole wafer at a time in order to facilitate large-scale data collection and statistical data analysis.

An object of an embodiment of the present invention is to provide a method and system which renders photoemission analysis effective as a yield management tool.

Briefly, and in accordance with at least one of the foregoing objects, an embodiment of present invention provides a method and system for collecting and analyzing photoemission data wherein illumination and photoemission images are acquired for a plurality of die, such as for each die on a wafer. Then, the images are overlaid, aligned, and assembled in a mosaic, thereby allowing analysis of the photoemission occurring across a plurality of die, such as across the entire wafer. Preferably, gathering this data allows statistical analysis of the photoemission such as analysis of commonly emitting locations to identify structures/cells that are sensitive to the manufacturing process.

BRIEF DESCRIPTION OF THE DRAWINGS

The organization and manner of the structure and operation of the invention, together with further objects and advantages thereof, may best be understood by reference to the following description, taken in connection with the accompanying drawing, wherein.

DETAILED DESCRIPTION OF EMBODIMENTS OF THE INVENTION

Figure 1:
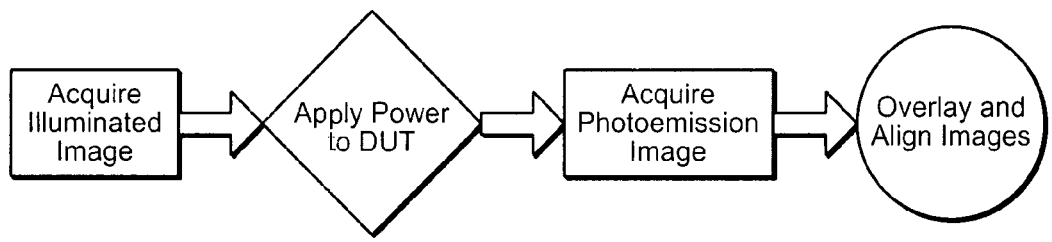
FIG. 1 illustrates dataflow associated with a prior art photoemission analysis technique.

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

Figure 2:
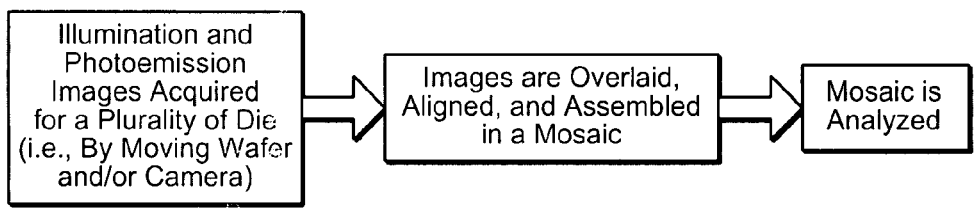
FIG. 2 illustrates dataflow associated with a photoemission analysis technique which is in accordance with an embodiment of the present invention.

The present invention applies to the wafer manufacturing process and involves collecting photoemission data for a whole wafer at a time in order to facilitate large-scale data collection and statistical data analysis. FIG. 2 illustrates the dataflow of a method of collecting and analyzing photoemission data, wherein the method is in accordance with an embodiment of the present invention. As shown, illumination and photoemission images are acquired for a plurality of die, such as for each die on a wafer. Then, the images are overlaid, aligned, and assembled in a mosaic. Finally, the mosaic is analyzed, thereby allowing analysis of the photoemission occurring across a plurality of die, such as across the entire wafer. Preferably, gathering this data allows statistical analysis of the photoemission such as analysis of commonly emitting locations to identify structures/cells that are sensitive to the manufacturing process.

When the images are acquired, preferably either the wafer and/or the camera used to acquire the images are moved such that the whole wafer is analyzed. The present invention focuses on collecting photoemission data on the whole wafer, rather than individual die. The process is repeated for each die on the wafer, and the imaging tool is stepped to the next die. The images collected for each die are then assembled in a mosaic, allowing analysis of the photoemission occurring across the entire wafer. Gathering this data allows statistical analysis of the photoemission, such as analysis of commonly emitting locations, to identify structures/cells that are sensitive to the manufacturing process.

Figure 3:
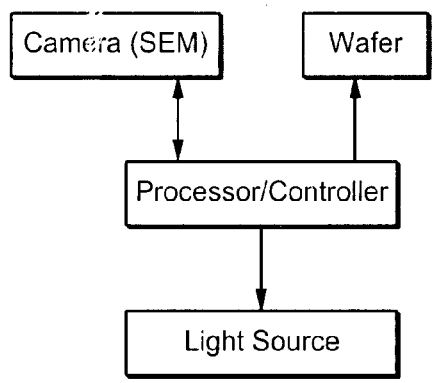
FIG. 3 provides a simplified block diagram of a photoemission analysis system which is in accordance with an embodiment of the present invention.

FIG. 3 illustrates a photoemission analysis system which is in accordance with an embodiment of the present invention. While the system may include additional components, FIG. 3 is simplified, and shows only those components which are relevant to the present invention. As shown, a processor/controller is in communication with a light source, a wafer (which includes a plurality of die) and a camera. In accordance with the method discussed above, the processor/controller is configured to operate the light source, operate the camera and receive data (i.e., images) therefrom, overlay and align the images, arrange the images into a mosaic, and analyze the mosaic. The processor/controller is configured to move the camera, the wafer, or both to acquire the images. The processor/controller may be provided as a single structure, or a plurality of separate structures which may be connected to or in communication with each other.

The present invention provides that large amounts of photoemission data on the wafer as a whole is gathered. The present invention provides that spatial relationships are maintained between die photoemission images, and that electrical stating of the die is automatically controlled. The present invention also preferably provides for automated stepping from die-to-die allows photoemission analysis, thereby serving as a large-scale data acquisition system that plays a significant role in managing semiconductor manufacturing yields.

The present invention treats photoemission on a wafer level. The present invention provides that photoemission is performed on all die on the wafer, in an automated fashion, greatly reducing the analysis time and amount of effort required to collect this volume of data. The benefits of collecting large volumes of photoemission include an increased yield learning toolbox and the ability to perform statistical analysis on photoemission sites, both by location and by intensity, to be used as a yield learning/defect characterization tool.

The present invention enhances the current manufacturing process by allowing large volumes of photoemission data to be collected. Current techniques and equipment do not allow for volume data collection, and are very time intensive. The present invention covers automating the photoemission process. This automation allows for a large volume of photoemission data to be collected and analyzed, creating a new class of data that is useable in conjunction with existing data for yield improvement.

While embodiments of the present invention are shown and described, it is envisioned that those skilled in the art may devise various modifications of the present invention without departing from the spirit and scope of the appended claims.

What is claimed is:

1. A method of collecting and arranging photoemission data relating to a plurality of die on a wafer, said method comprising: acquiring and collecting illumination and photoemission images for each one of a plurality of die on the wafer; and overlaying, aligning, and assembling the collected images into a mosaic, wherein spatial relationships between the plurality of die are maintained when forming the mosaic.

2. A method as recited in claim 1, further comprising analyzing the mosaic.

3. A method as recited in claim 1, further comprising moving the wafer to acquire the images relating to the plurality of die.

4. A method as recited in claim 1, further comprising providing a camera and moving the camera to acquire the images relating to the plurality of die.

5. A method as recited in claim 1, further comprising providing a camera and moving the camera and wafer to acquire the images relating to the plurality of die.

6. A system for collecting and arranging photoemission data relating to a plurality of die on a wafer, said system comprising: a camera configured to acquire and collect illumination and photoemission images of the die; a processor/controller in communication with the camera, said processor/controller configured to operate the camera to acquire and collect illumination and photoemission images for each one of a plurality of die on the wafer, and configured to overlay, align, and assemble the collected images into a mosaic, wherein spatial relationships between the plurality of die are maintained when forming the mosaic.

7. A system as recited in claim 6, wherein the processor/controller is configured to analyze the mosaic.

8. A system as recited in claim 6, wherein the processor/controller is configured to move the camera to acquire the images relating to the plurality of die.

9. A system as recited in claim 6, wherein the processor/controller is configured to move the wafer to acquire the images relating to the plurality of die.

10. A system as recited in claim 6, wherein the processor/controller is configured to move the camera and wafer to acquire the images relating to the plurality of die.

* * * * *